(12) United States Patent
Paul (10) Patent No.: US 11,771,545 B2
(45) Date of Patent: Oct. 3, 2023

(54) PROSTHESIS FOR TRACHEA

(71) Applicant: Subroto Paul, New York, NY (US)

(72) Inventor: Subroto Paul, New York, NY (US)

(73) Assignee: Subroto Paul, New York, NY (US)

( * ) Notice: Subject to any disclaimer, the term of this patent is extended or adjusted under 35 U.S.C. 154(b) by 560 days.

(21) Appl. No.: 16/883,438

(22) Filed: May 26, 2020

(65) Prior Publication Data

US 2021/0145562 A1    May 20, 2021

Related U.S. Application Data

(60) Provisional application No. 62/937,711, filed on Nov. 19, 2019.

(51) Int. Cl.
*A61F 2/04* (2013.01)

(52) U.S. Cl.
CPC .......... *A61F 2/04* (2013.01); *A61F 2002/046* (2013.01); *A61F 2220/0016* (2013.01); *A61F 2230/0043* (2013.01)

(58) Field of Classification Search
CPC .................. A61F 2/04; A61F 2002/046; A61F 2220/0016; A61F 2230/0043; A61F 2220/0041; A61F 2250/0004
See application file for complete search history.

(56) References Cited

U.S. PATENT DOCUMENTS 5,749,916 A * 5/1998 Richelsoph ............. A61F 2/446
606/907

* cited by examiner

*Primary Examiner* — Yashita Sharma (57) ABSTRACT

A prosthesis for attachment to an external surface of a trachea and support a membranous portion of the trachea is disclosed. The prosthesis includes a first member, a second member and a biasing member engaged with the first member and the second member. The first member has at least one first tooth adapted to be inserted inside the membranous portion. The second member is movably coupled to the first member and includes at least one second tooth disposed substantially opposite to the at least one first tooth. The at least second tooth is configured to be inserted inside the membranous portion. The biasing member biases the first member relative to the second member to a first position. The first member and the second member are disposed away from the first position when engaged with the trachea applying a tension force on the membranous portion.

3 Claims, 8 Drawing Sheets

PROSTHESIS FOR TRACHEA

TECHNICAL FIELD

The disclosure relates generally to a prosthesis for opening a trachea. More particularly, the disclosure relates to a prosthesis suitable for externally stent open a trachea and proximal right and left mainstem airway to minimize a collapse of a membranous airway and a method of attaching the prosthesis to the trachea.

BACKGROUND

Bronchotracheomalacia is characterized by segmental or diffuse tracheal or bronchial weakness. It can occur due to softening of the cartilage or dynamic collapse of the membranous airway (excessive forward motion of the membranous posterior wall of the tracheobronchial tree). Both conditions result in narrowing of the tracheobronchial lumen during expiration.

Symptoms due to the collapse are shortness of breath, cough, recurrent infection, and respiratory failure. Treatment depends on the extent of symptoms. Treatments vary and include positive pressure ventilation, internal stenting, tracheostomy, and open surgery (tracheoplasty). In a tracheoplasty, mesh is used to reinforce the membranous portion of the trachea. Other techniques involve attaching grafts to support the trachea or membranous trachea. Internal stenting can lead to granulation tissue within the airway leading to airway obstruction. Tracheostomy leads to the need for a permanent external appliance out of the neck. Tracheoplasty requires open surgery with often large incisions and general anesthesia.

SUMMARY

According to an aspect of the disclosure a prosthesis is disclosed. The prosthesis is attached to an external surface of a trachea and configured to support a membranous portion of the trachea. The prosthesis includes a first member, a second member and a biasing member engaged with the first member and the second member. The first member has at least one first tooth adapted to be inserted, at least partially, inside the membranous portion. The second member is movably coupled to the first member and includes at least one second tooth disposed substantially opposite to the at least one first tooth, the at least second tooth is configured to be inserted, at least partially, inside the membranous portion. The biasing member is adapted to bias the first member relative to the second member to a first position. The first member and the second member are disposed away from the first position when engaged with the trachea and apply a tension force on the membranous portion.

In an embodiment, the second member is pivotally coupled to the first member.

In an embodiment, the each of the first member and the second member includes an L-shape.

In an embodiment, the biasing member is a spring.

In an embodiment, the prosthesis further includes a screw adapted to hold the first member in a position away from the first position.

In an embodiment, the prosthesis further includes a screw engaged with the first member and adapted to facilitate the pivotal movement of the first member relative to the second member.

In an embodiment, the first tooth is adapted to move towards the second tooth in response to a rotation of the screw in a first direction and move away from the second tooth in response to a rotation of the screw in a second direction.

In an embodiment, the first member and the second member are moved towards each other by applying a compressive force on at least one of the first member or the second member.

In an embodiment, the biasing member is an elastic body extending from the first member to the second member.

According to an aspect of the disclosure a method for insertion and attachment of a prosthesis with a trachea having a cartilage and a membranous portion is disclosed. The method includes making an incision into a neck of a patient to access the trachea. The method further includes inserting a mediastinoscope through the incision and dissecting an anterior trachea and a medial trachea. The prosthesis is inserted through the incision by using a sliding scope and the prosthesis is attached to an external surface of the trachea. The prosthesis includes a first member, a second member and a biasing member engaged with the first member and the second member. The first member has at least one first tooth adapted to be inserted, at least partially, inside the membranous portion. The second member is movably coupled to the first member and includes at least one second tooth disposed substantially opposite to the at least one first tooth, the at least second tooth is configured to be inserted, at least partially, inside the membranous portion. The biasing member is and adapted to bias the first member relative to the second member to a first position. The first member and the second member are disposed away from the first position when engaged with the trachea and apply a tension force on the membranous portion.

In an embodiment, attaching the prosthesis includes moving at least one first tooth and at least one second tooth towards each other. The method further includes inserting the at least one first tooth and the at least one second tooth into the trachea such that the at least one first tooth and the at least one second tooth pass through the cartilage and engage with the membranous portion.

In an embodiment, the first member and the second member are moved towards each other by applying a compressive force on at least one of the first member or the second member.

In an embodiment, the incision is a suprasternal incision.

In an embodiment, the second member is pivotally coupled to the first member.

In an embodiment, the each of the first member and the second member includes an L-shape.

In an embodiment, the biasing member is a spring.

In an embodiment, the prosthesis further includes a screw adapted to hold the first member in a position away from the first position.

In an embodiment, the prosthesis further includes a screw engaged with the first member and adapted to facilitate the pivotal movement of the first member relative to the second member.

In an embodiment, the first tooth is adapted to move towards the second tooth in response to a rotation of the screw in a first direction and move away from the second tooth in response to a rotation of the screw in a second direction.

In an embodiment, the biasing member is an elastic body extending from the first member to the second member.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Also, wherever possible, the same reference numbers will be used throughout the drawings to refer to the same or the like parts.

Figure 1:
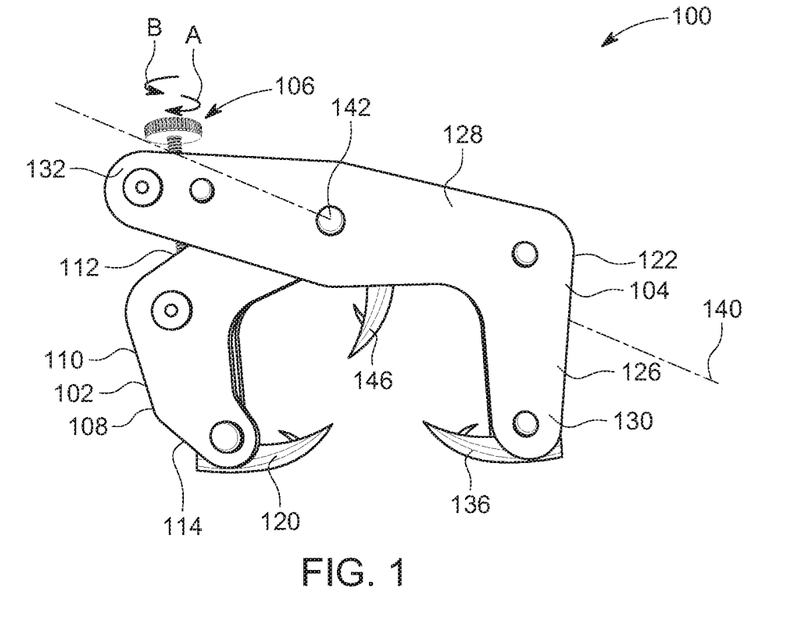
FIG. 1 illustrates a front view of a prosthesis, in accordance with an embodiment of the disclosure.
Figure 2:
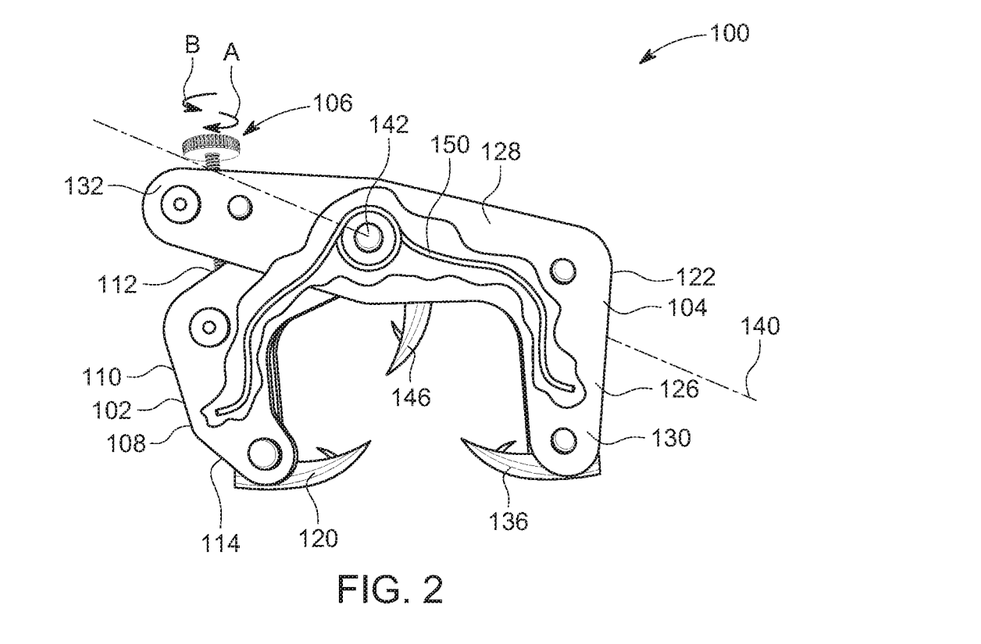
FIG. 2 illustrates a front perspective view of the prosthesis of FIG. 1 showing a biasing member in a cut-out, in accordance with an embodiment of the disclosure
Figure 3:
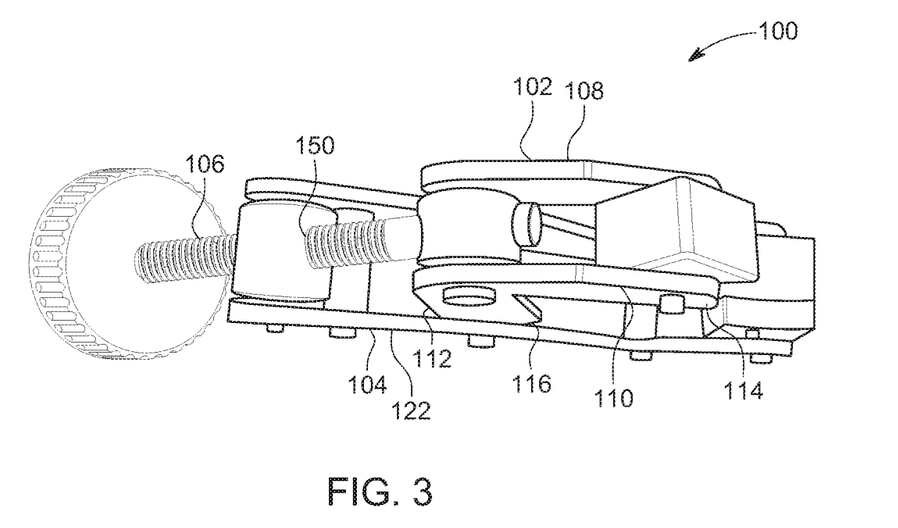
FIG. 3 illustrates a top perspective view of the prosthesis, in accordance with an embodiment of the disclosure.
Figure 4:
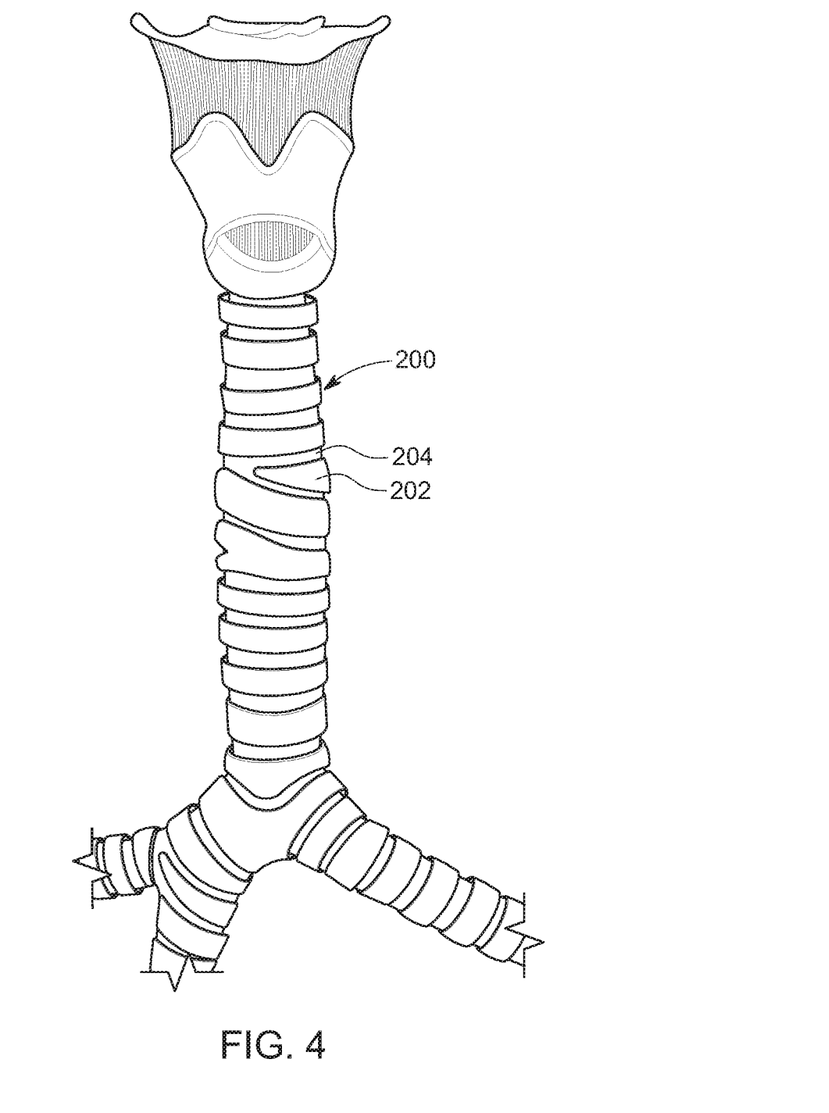
FIG. 4 illustrates a trachea, in accordance with an embodiment of the disclosure.
Figure 5:
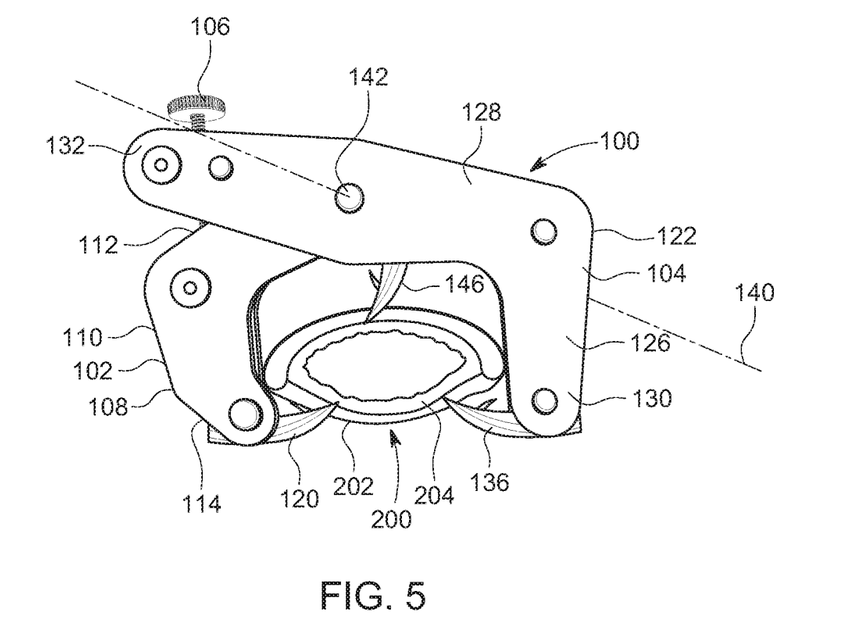
FIG. 5 illustrates the prosthesis in engagement with a membranous portion of the trachea, in accordance with an embodiment of the disclosure.

Referring to FIGS. 1, 2 and 3 an exemplary prosthesis 100 suitable for attachment to a trachea 200 (shown in FIGS. 3 and 4) is shown. The prosthesis 100 is adapted for attachment to an external surface of the trachea 200, for example, to a cartilage 202 of the trachea 200, and contacts and pulls a membranous portion 204 outwardly. As shown in FIGS. 4 and 5, the membranous portion 204 defines an inner layer of the trachea 200, while the cartilage 202 defines an outer layer of the trachea 200 and supports the membranous portion 204. Therefore, the cartilage 202 holds the membranous portion 204, and thereby keeps the membranous portion 204 from collapsing.

Again referring to FIGS. 1, 2 and 3, the prosthesis 100 includes a first member 102, a second member 104 pivotally/movably coupled to the first member 102, a biasing member 150 (shown in FIG. 2) coupled to the first member 102 and the second member 104 and configured to bias the first member 102 to a first position, and a screw 106 engaged with the first member 102 and the second member 104 to move the first member 102 away from the first position. As shown, the first member 102 may include a first elongated member 108 having a substantially L shape having a first portion 110 and a second portion 112 attached to the first portion 110 and disposed at an angle relative to the first portion 110. In an embodiment, the angle between the first portion 110 and the second portion 112 may lie between 75 degrees to 105 degrees. Further, the first member 102 includes a first end 114 and a second end 116 (shown in FIG. 3). The first portion 110 may extend from the first end 114 to the second portion 112, while the second portion 112 may extend from the first portion 110 to the second end 116. As shown, the first member 102 may include a first tooth 120 disposed at the first end 114 and coupled to the first end 114 (i.e. the first portion 110). In an embodiment, the first tooth 120 is adapted to move/pivot relative to the first elongated member 108 to facilitate an insertion/engagement of the first tooth 120 to the trachea 200.

Similar to the first member 102, the second member 104 may include a second elongated member 122 having an L shape and having a third portion 126 and a fourth portion 128 attached to the third portion 126 and disposed at an angle relative to the third portion 126. In an embodiment, an angle between the third portion 126 and the fourth portion 128 may lie between 75 degrees to 105 degrees. Further, the second member 104 includes a first end 130 and a second end 132, and the third portion 126 extends from the first end 130 to the fourth portion 128, while the fourth portion 128 may extend from the third portion 126 to the second bend 132. As shown, the second member 104 may include a second tooth 136 disposed at the first end 130 and coupled to the third portion 126. In an embodiment, the second tooth 136 is adapted to move/pivot relative to the third portion 126 to facilitate an insertion/engagement of the second tooth 136 into the trachea 200.

As shown, the second portion 112 and the fourth portion 128 are pivotally coupled to each other and adapted to pivot about a pivot axis 140. A pivoting motion of the second portion 112 relative to the fourth portion 128 may cause a movement of the first tooth 120 towards or away from the second tooth 136. The fourth portion 128 and the second portion 112 may be pivotally attached by inserting a pin 142 through the holes defined in the second portion 112 and the fourth portion 128. Further, the prosthesis 100 may include a third tooth 146 disposed between the first tooth 120 and the second tooth 136 and attached to fourth portion 128 or the pin 142. The teeth 120, 136, 146 are adapted to contact the membranous portion 204 and hold the membranous portion 204 in an expanded position to prevent the membranous portion 204 from collapsing, therefore closing the airway.

Furthermore, in an embodiment, the screw 106 is coupled to the first member 102 and the second member 104 and adapted to move/pivot the first member 102 relative to the second member 104. In an embodiment, the screw 106 may be coupled to the second end 132 of the second member 104 and may pass through a threaded hole 150 formed into the second member 104, while an end of the screw 106 may be adapted to be engaged with the first end 114 of the first member 102. In an embodiment, when the screw is rotated, the screw 106 may contact the first end 114 and applies a force on the first end 114 of the first member 102 to move/pivot the first member 102 relative to the second member 104. Accordingly, the first end 114 of the first member 102, and hence the first tooth 120, moves toward the second tooth 136 upon a rotation of the screw 106 in a first direction 'A', while a rotation of the screw 106 in a second direction 'B' opposite to the first direction 'A' may cause the movement of the first end 114 of the first member 102 away from the first end 130 of the second member 104. In this manner, the rotation of the screw 106 facilitates a pivotal movement of the first member 102 relative to the second member 104. In an embodiment, the biasing member, for example a spring, may be connected to the first member 102 and the second member 104. The biasing member is adapted to bias the first member 102 to the first position and applies a force on the first member 102 when the first member 102 (i.e. the first end 114) moves away from the first position to bring the first end 114 (i.e. the first member 102) to the first position.

Figure 6:
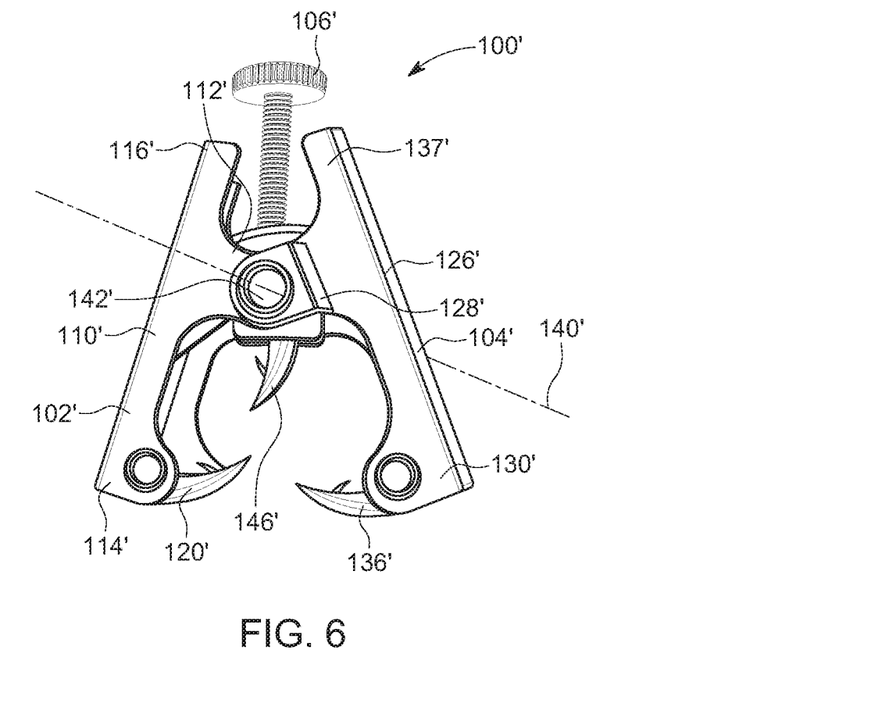
FIG. 6 illustrates a prosthesis, in accordance with an alternative embodiment of the disclosure.
Figure 7:
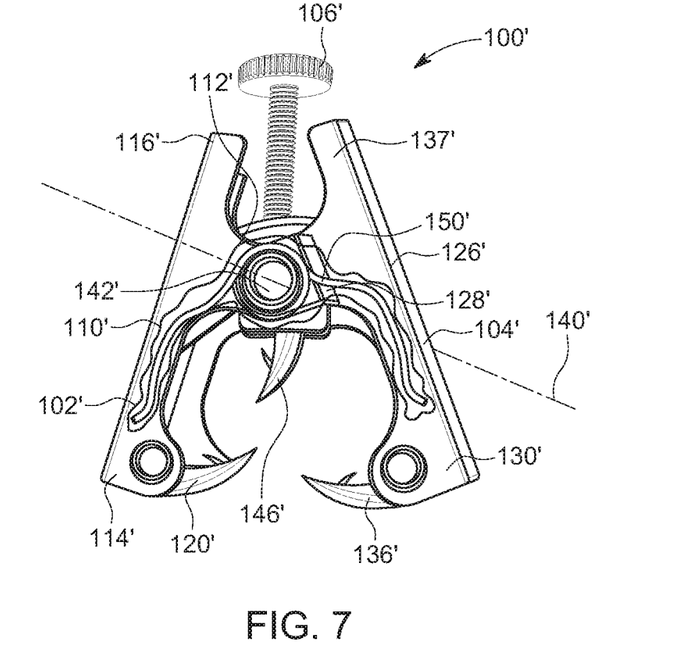
FIG. 7 illustrates the prosthesis of FIG. 6 showing a biasing member in a cut-out, in accordance with an alternative embodiment of the disclosure.

Referring to FIGS. 6 and 7, a prosthesis 100' according to an alternative embodiment is shown. the prosthesis 100' includes a first member 102', a second member 104' pivotally coupled to the first member 102', a biasing member 150' (shown in FIG. 7)) coupled to the first member 102' and the second member 104' and configured to bias the first member 102' and the second member 104' to a first position, and a screw 106' engaged with the first member 102' and the second member 104' to hold the first member 102' and the second member 104' in a position other than the first position against a biasing force of the biasing member. As shown, the first member 102' includes a first end 114', a second end 116', an elongated portion 110' (i.e. first portion 110') extending from the first end 114' to the second end 116', and a second portion 112' disposed proximate to the second end 116' and extending substantially perpendicular to the elongated portion 110'. The second portion 112' is pivotally connected to the second member 104'. Further, as shown, the first member 102' may include a first tooth 120' disposed at the first end 114' and coupled to the first end 114' (i.e. the first portion 110'). In an embodiment, the first tooth 120' is adapted to move relative to the first portion 110' to facilitate an insertion/engagement of the first tooth 120' to the trachea 200.

Similar to the first member 102', the second member 104' may include a first end 130', a second end 132', an elongated portion 126' (i.e. third portion 126') extending from the first end 130' to the second end 132', and a fourth portion 128' disposed proximate to the second end 132' and extending substantially perpendicularly to the elongated portion 126'. The fourth portion 128' is pivotally connected to the second portion 112'. Further, as shown, the second member 104' may include a second tooth 136' disposed at the first end 130' and coupled to the first end 130' (i.e. the third portion 126'). In an embodiment, the second tooth 136' is adapted to move relative to the third portion 126' to facilitate an insertion/engagement of the second tooth 136' to the trachea 200.

As shown, the second portion 112' (i.e. the first member 102') and the fourth portion 128' (i.e. the second member) are pivotally coupled to each other and adapted to pivot about a pivot axis 140'. A pivoting motion of the first member 102' and the second member 104' may cause a movement of the first tooth 120' and the second tooth 136' towards or away from each other. The fourth portion 128' and the second portion 112' may be pivotally attached by inserting a pin 142' through the holes (not shown) defined in the second portion 112' and the fourth portion 128'. Further, the prosthesis 100' may include a third tooth 146' disposed between the first tooth 120' and the second tooth 136' and attached to the pin 142'. The teeth 120', 136', 146' are adapted to contact and engage with the membranous portion 204 and hold the membranous portion 204 in an expanded position.

Furthermore, in the first position, the first end 114' of the first member 102' is disposed at a distance from the first end 130' of the second member 104, thereby defining a gap 'G" therebetween. The first end 114' of the first member 102' and the first end 130' of the second member 104' are adapted to move towards each other in response to an application of force on the first member 102' and the second member 104'. In this manner, the gap "G' between the first end 114' and the first end 130' is reduced. To hold a relative positioning of the first end 114' and the first end 130', the screw 106' is rotated and engaged with the first member 102' and the second member 104' such that the screw 106' restrains or prevents any pivotal motion of the first member 102' and the second member 104' upon removal of the force.

Figure 8:
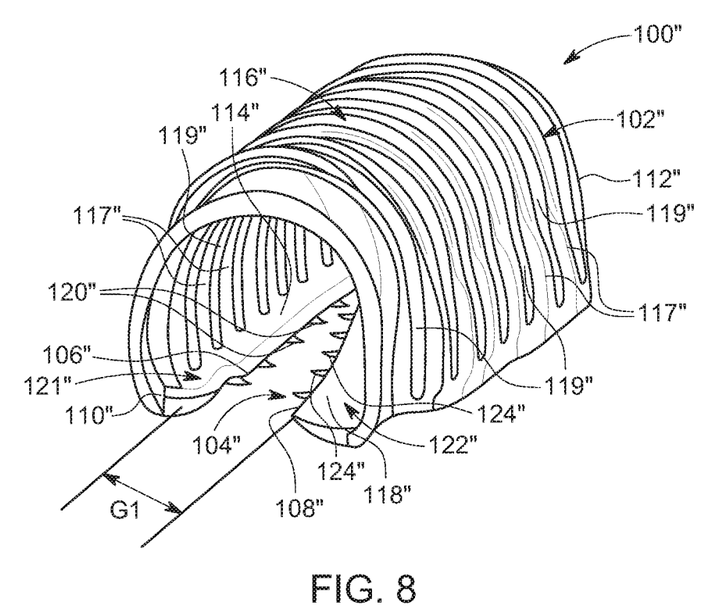
FIG. 8 illustrates a prosthesis, in accordance with a yet another embodiment of the disclosure.

Referring to FIG. 8, a prosthesis 100' according to yet another embodiment is disclosed. The prosthesis 100" may include a body 102' having a longitudinal cut out 104" defining a first edge 106" and a second edge 108" disposed substantially parallel to the first edge 106" and facing the first edge 106". As shown, the first edge 106" and the second edge 108", each extends from a first longitudinal end 110" to a second longitudinal end 112" and defines a gap 'G1' therebetween. Further, the body 104' may include a first edge portion 114" (also referred to as first elongated portion 114"), a biasing portion 116" (also referred to as biasing member 116"), and a second edge portion 118" (also referred to as second elongated portion 118"). The first elongated portion 114" extends from the first edge 106" to the biasing portion 116", while the second elongated portion 118" extends from the second edge 108" to the biasing portion 116". Accordingly, the biasing portion 116" extends from the first elongated portion 114" to the second elongated portion 118", thereby is engaged with the first elongated portion 114" and the second elongated portion 118". As shown, the biasing portion 116" may include a plurality of ribs 117" arrayed between the first longitudinal end 110" and the second longitudinal end 112". The plurality of ribs 117" is arranged spaced apart from each other, defining a plurality of channels 119" therebetween. Due to the presence of the ribs 117" and the channels 119", the biasing member 116" may provide an elasticity to prosthesis 100". In an embodiment, the biasing member 116" may include a material having elastic properties. Accordingly, the biasing member 116" provides an elastic body portion to facilitate a movement of the first edge 106" and the second edge 108" towards each other in response to application of force and thereby reducing the gap. It may be appreciated that due to elasticity of the body 102" or the biasing member 114", the first edge 106" and the second edge 108" may move away from each other to respective original position (i.e. first position) upon a removal of the force.

Further, the prosthesis 100" includes a plurality of first teeth 120" arrayed linearly along the first edge 106" and disposed spaced apart from each other. Each of the first teeth 120" extends outwardly from the first edge 106" and into the gap 'G1'. The first elongated portion 114" and the plurality of first teeth 120" together define a first member portion 121" (also referred to as first member 121") of the prosthesis 100". Further, the prosthesis 100" includes a plurality of second teeth 124" arrayed linearly along the second edge 108" and spaced apart from each other. Each of the second teeth 124" extends outwardly from the second edge 108" and into the gap 'G1'. The second elongated portion 118" and the plurality of second teeth 124" together define a second member portion 122" (also referred to as second member 122") of the prosthesis 100". The first teeth 120" and the second teeth 124" are adapted to engage with the membranous portion 204 and/or the cartilage 202 to reinforce the membranous portion 204 and thereby preventing a closure of the airway. In an embodiment, the teeth 120", 124" are moved towards each other by applying a compressive force on the body 102" before engaging the teeth 120", 124" with the trachea 200. Upon engaging the teeth 120", 124" with the trachea 200 (i.e. the membranous portion 204), the compressive force is released. Accordingly, the first teeth 120" and the second teeth 124" tend to move away from each other, thereby applying a force on the membranous portion 204 and/or the cartilage 202 to keep the airway open. In this manner, the second member portion 118" and the first member portion 114" are movably coupled to each other and biased in a first position by the biasing portion 116".

A method of insertion and attachment of the prosthesis 100 with the trachea 200 is now discussed. It may be appreciated the prosthesis 100', 100" may similarly be attached with the trachea 200. For inserting the prosthesis 100 inside a human body, a surgeon may first make a small incision into a neck of a patient to access the trachea 200 of the patient. In an embodiment, the incision may be a suprasternal incision. Subsequently, the surgeon may insert a mediastinoscope through the incision and dissects an anterior trachea and a medial trachea. Thereafter, the prosthesis 100 may be inserted through the incision by using a sliding scope and attached to the trachea 200. For attaching the prosthesis 100 to the trachea 200, the prosthesis 100 is moved/compressed by applying a force such that the first tooth 120 and the second tooth 136 are disposed closer to each other than a default position (i.e. the first position). Thereafter, the teeth 120, 136 are inserted into the trachea 200 such that the teeth 120, 136 pass through the cartilage 202 and engage with the membranous portion 204. As shown, in the engaged position, tips of the teeth 120, 136, 146 are disposed proximate to a junction of the cartilage 202 and the membranous portion 204. The teeth 120, 137 of the prosthesis 100 applies a pull force on the membranous portion 204 in a radial direction to open the airway due to the biasing force of the biasing member or the elastic body. In this manner, the prosthesis 100 is attached to the trachea 200 from outside and by creating a small incision in the neck of the patient. The disclosure, therefore, allows for a minimally invasive means of adjustable external support of the airway. The prosthesis 2100 is made of inert materials or biodegradable material and can be removed.

What is claimed is:

1. A prosthesis for attachment to an external surface of a trachea and configured to support a membranous portion of the trachea, the prosthesis comprises:

a first member having at least one first tooth adapted to be inserted, at least partially, inside the membranous portion;

a second member movably coupled to the first member and including at least one second tooth disposed substantially opposite to and facing the at least one first tooth, the at least second tooth is configured to be inserted, at least partially, inside the membranous portion, wherein the at least one first tooth and the at least second tooth extend toward each other and are disposed inside a gap defined between the first member and the second member; and a biasing member engaged with the first member and the second member and adapted to bias the first member and the second member to a first position, the biasing member includes a plurality of ribs arrayed in a longitudinal direction and arranged spaced apart from each other, wherein the first member and the second member are moved toward each other from the first position to engage the at least one first tooth and at least one second tooth with the trachea to apply a tension force on the membranous portion to keep an airway of the trachea open.

2. The prosthesis of claim 1, wherein the first member and the second member are moved towards each other by applying a compressive force on at least one of the first member or the second member.

3. The prosthesis of claim 1, wherein the biasing member is an elastic body extending from the first member to the second member.

* * * * *